(12) United States Patent
Fu et al.

(10) Patent No.: US 7,268,359 B2
(45) Date of Patent: Sep. 11, 2007

(54) APPARATUS AND METHOD FOR TRANSPORTING RADIOPHARMACEUTICALS

(75) Inventors: Monty Mong Chen Fu, Chatsworth, CA (US); Bing Bing Zhu, Stevensons Ranch, CA (US)

(73) Assignee: Cardinal Health, Inc., Dublin, OH (US)

( * ) Notice: Subject to any disclaimer, the term of this patent is extended or adjusted under 35 U.S.C. 154(b) by 0 days.

(21) Appl. No.: 11/184,291

(22) Filed: Jul. 18, 2005

(65) Prior Publication Data

US 2005/0247893 A1    Nov. 10, 2005

Related U.S. Application Data

(63) Continuation of application No. 10/310,353, filed on Dec. 4, 2002.

(60) Provisional application No. 60/338,355, filed on Dec. 5, 2001.

(51) Int. Cl.
*G21F 5/00* (2006.01)

(52) U.S. Cl. .............................. 250/507.1; 250/506.1; 206/365

(58) Field of Classification Search ............. 250/515.1, 250/507.1, 506.1; 378/19
See application file for complete search history.

(56) References Cited

U.S. PATENT DOCUMENTS

| | | | |
|---|---|---|---|
| 1,931,798 A * | 10/1933 | Hundt | ................. 220/62.15 |
| 2,682,352 A | 6/1954 | Hawkins et al. | |
| 2,812,231 A | 11/1957 | Zar | |
| 3,074,542 A | 1/1963 | Myerson et al. | |
| 3,101,841 A | 8/1963 | Baldwin | |
| 3,149,717 A | 9/1964 | Castelli | |
| 3,272,322 A | 9/1966 | Ogle | |
| 3,294,231 A | 12/1966 | Vanderbeck | |
| D208,080 S | 7/1967 | Hamilton | |
| 3,329,146 A | 7/1967 | Waldman, Jr. | |
| 3,344,787 A | 10/1967 | Maclean | |
| 3,367,488 A | 2/1968 | Hamilton | |

(Continued)

*Primary Examiner*—Nikita Wells
*Assistant Examiner*—Johnnie L Smith, II
(74) *Attorney, Agent, or Firm*—Sheppard, Mullin, Richter & Hampton LLP (57) ABSTRACT

A method and apparatus for transporting radiopharmaceuticals. Typically, the apparatus is a two-part assembly, each part having an exterior shell, a radiation shield and a non-porous lining. Additionally, the assembled apparatus has a sealed internal chamber suitable for carrying a syringe or a sharps container containing a syringe. The internal chamber of the radiopharmaceutical pig is lined with a non-porous lining, typically a durable plastic, that prevents contamination of the radiopharmaceutical doses, the radiation shield, or the environment. Additionally, the non-porous lining can be quickly and easily cleaned and sterilized, avoiding the often difficult, to impossible, task of cleaning and sterilizing the radiation shield of the radiopharmaceutical pig. The non-porous lining is surrounded by a radiation shield that is typically comprised of elemental lead. The radiation shield prevents radiation from the radiopharmaceutical from contaminating the user or environment. The radiation shield is surrounded by an exterior shell that absorbs impact and prevents the radiopharmaceutical pig from breaking. Additionally, the exterior shell prevents environmental exposure to the potentially hazardous material of the radiation shield. Generally, a method of transporting a radiopharmaceutical by filling the container with a radiopharmaceutical, inserting the container into the internal chamber of the radiopharmaceutical pig having a non-porous lining, and assembling the radiopharmaceutical pig so the that the container is in the internal chamber and is encapsulated by the radiation shield, is also provided.

20 Claims, 6 Drawing Sheets

U.S. PATENT DOCUMENTS

| | | | |
|---|---|---|---|
| 3,531,644 A | 9/1970 | Koster | |
| 3,673,411 A | 6/1972 | Glasser | |
| 3,677,247 A | 7/1972 | Brown | |
| 3,882,315 A | 5/1975 | Soldan | |
| 3,971,955 A | 7/1976 | Heyer et al. | |
| 4,081,688 A | 3/1978 | Fries | |
| 4,106,622 A | 8/1978 | Windischman | |
| 4,113,090 A | 9/1978 | Carstens | |
| 4,357,541 A | 11/1982 | Ernst | |
| 4,626,380 A * | 12/1986 | Baatz et al. | 250/506.1 |
| 4,781,697 A | 11/1988 | Slaughter | |
| 4,846,235 A | 7/1989 | Handke | |
| 4,851,702 A | 7/1989 | Perlman | |
| 4,869,299 A | 9/1989 | Handke | |
| 4,892,525 A | 1/1990 | Hermann, Jr. et al. | |
| 4,917,263 A | 4/1990 | Korb | |
| D324,101 S | 2/1992 | Reif et al. | |
| 5,096,062 A | 3/1992 | Burkhardt et al. | |
| 5,099,998 A | 3/1992 | Curzon et al. | |
| 5,145,063 A | 9/1992 | Lee | |
| 5,157,900 A | 10/1992 | Kupersmit | |
| D333,347 S | 2/1993 | Kemp et al. | |
| 5,205,408 A | 4/1993 | Cobb | |
| 5,235,795 A | 8/1993 | DeBusk | |
| 5,245,117 A | 9/1993 | Withers et al. | |
| 5,277,312 A | 1/1994 | Vumbaca | |
| 5,303,836 A | 4/1994 | Childress | |
| 5,323,719 A | 6/1994 | Withers et al. | |
| 5,385,105 A | 1/1995 | Withers, Jr. et al. | |
| 5,417,326 A | 5/1995 | Winer | |
| 5,519,931 A * | 5/1996 | Reich | 29/426.3 |
| 5,536,945 A * | 7/1996 | Reich | 250/507.1 |
| 5,552,612 A | 9/1996 | Katayama et al. | |
| 5,611,429 A | 3/1997 | Phillips | |
| 5,672,883 A * | 9/1997 | Reich | 250/507.1 |
| 5,828,073 A | 10/1998 | Zhu et al. | |
| 5,834,788 A | 11/1998 | Fu et al. | |
| D405,609 S | 2/1999 | Fu et al. | |
| 5,918,443 A | 7/1999 | Phillips | |
| 5,927,351 A | 7/1999 | Zhu et al. | |
| RE36,693 E * | 5/2000 | Reich | 250/507.1 |
| D425,197 S | 5/2000 | Comer et al. | |
| 6,162,198 A | 12/2000 | Coffey et al. | |
| 6,199,699 B1 | 3/2001 | Eastman | |
| D447,231 S | 8/2001 | Chen Fu et al. | |
| 6,425,174 B1 * | 7/2002 | Reich | 29/469 |
| 6,576,918 B1 | 6/2003 | Fu et al. | |
| 6,586,758 B2 * | 7/2003 | Martin | 250/515.1 |
| 6,722,499 B2 | 4/2004 | Reich | |
| 6,822,253 B1 * | 11/2004 | Martin et al. | 250/507.1 |
| 6,963,073 B2 | 11/2005 | Martin et al. | |
| 2002/0178566 A1 * | 12/2002 | Reich | 29/426.5 |
| 2002/0195575 A1 * | 12/2002 | Martin | 250/506.1 |
| 2003/0222228 A1 | 12/2003 | Fu et al. | |
| 2004/0016098 A1 * | 1/2004 | Reich | 29/428 |
| 2005/0198800 A1 * | 9/2005 | Reich | 29/426.3 |
| 2005/0234424 A1 * | 10/2005 | Besing et al. | 604/500 |

* cited by examiner

APPARATUS AND METHOD FOR TRANSPORTING RADIOPHARMACEUTICALS

This is a continuation of application Ser. No. 10/310,353, filed Dec. 4, 2002, which claims the benefit of U.S. Provisional Application No. 60/338,355, filed Dec. 5, 2001.

FIELD OF THE INVENTION

The present invention generally relates to shielded apparatuses and, more particularly, to an apparatus and method for transporting radiopharmaceuticals.

BACKGROUND OF THE INVENTION

In the health care industry and, more specifically, in the field of nuclear medicine, radioactive materials known as radiopharmaceuticals are used in various applications, including non-invasive imaging of patients for various diagnostic, as well as therapeutic purposes. Over the years, the health care industry has developed many different radiopharmaceuticals designed to facilitate such applications.

Radiopharmaceuticals should be handled carefully because of their radioactive nature. Recognizing the need to carefully handle radioactive materials, various governmental agencies, including the U.S. Department of Transportation, the Nuclear Regulatory Commission (NRC), the Department of Transportation (DOT), and the Occupational Health and Safety Administration (OSHA), have promulgated regulations to ensure that they are handled safely. To avoid some of the overhead costs associated with addressing the above concerns, many hospitals have resorted to using outside pharmacy companies having expertise in the compounding and handling of radiopharmaceuticals to provide them with their radioactive drugs.

Typically, patients who require radioactive drugs require only a small dose of a specific drug. Therefore, if the number of patients generally requiring radioactive drugs is small, health care providers typically order radiopharmaceuticals in individual or "unit" doses for each specific patient. Furthermore, the radioactive agents in the drugs have various half lives and lose their effectiveness after a predetermined time period. Thus, if a hospital does not have the required demand, some of its unused radioactive agents may decay and become unusable. To avoid the expense of such in-house production of radioactive drugs, many hospitals now purchase each prescribed dose of a radioactive drug from an outside pharmacy.

The pharmacies which provide radioactive drugs to hospitals utilize the principles of mass production to reduce their per-unit costs. The pharmacies receive prescription orders and deliver the corresponding radioactive drugs to nearby hospitals. Each prescription is individually filled, and each dose of radioactive drug is packaged in a syringe intended for a specific patient. The syringes containing the radioactive drugs must be carefully handled and delivered inside containers offering some degree of radiation shielding. Furthermore, government regulations require syringes to be disposed of in a container that shields others from the risk of injury posed by their sharp hypodermic needles. Such a container, generally referred to as a "sharps" container, typically has an internal cavity or chamber that can hold at least one syringe. One type of sharps container has a chamber sealed by a spring-biased pivoting gate to keep syringes safely inside.

Conventionally, each dose of radioactive drug is packaged in a syringe intended for a specific patient, and transported and handled within a reusable apparatus having a radiation shield, commonly known as a radiopharmaceutical pig. The radiopharmaceutical pig typically is a two-part assembly, with an upper portion removably attached to the lower portion. Once the pig is assembled, it includes a sealed internal chamber suitable for carrying a syringe. The internal chamber of the radiopharmaceutical pig is surrounded by a radiation shield that is typically made of elemental lead. The heavy lead particles provide the desired radiation shielding. The radiation shield can be surrounded by an exterior shell, which typically is made of a polystyrene plastic. The exterior shell prevents damage to the radiopharmaceutical pig by absorbing any impact to it. By acting as a barrier between the radiation shield and the environment, the exterior shell also prevents lead particles from the radiation shield from contaminating the environment.

Once the syringe containing radioactive drugs is ready to be transported, it is placed into the internal chamber of the bottom portion of the radiopharmaceutical pig. The radiopharmaceutical pig is then assembled by removably attaching the top portion of the pig to the bottom portion of the pig. The assembled pig is then transported to the desired destination with the interior chamber containing the syringe and the radioactive drug.

Once the radiopharmaceutical pig containing the syringe and radioactive drug has arrived to its destination and the radioactive drug is ready to be used, the pig is disassembled and the syringe is removed. The dose is then injected into the patient, as needed. Once the syringe has been used, it is generally referred to as "spent," but usually contains at least a small amount of residual radioactive drug. Additionally, the hypodermic needle of the spent syringe is now biologically contaminated from coming into contact with the patient. The contaminated spent syringe is then put back into the bottom portion of the radiopharmaceutical pig. The top portion of the radiopharmaceutical pig is then removably attached, usually by interlocking threads, to the bottom portion of the pig. Once the top and bottom portions of the radiopharmaceutical pig are removably attached to one another, the radiopharmaceutical pig is sent back to the pharmacy for proper disposal of the contaminated spent syringe.

Using the radiopharmaceutical pig apparatus and method described above has certain drawbacks. One such drawback is the additional expense and hazard that arises from contaminating the radiopharmaceutical pig. The spent syringe is often placed back into the radiopharmaceutical pigs with the needle uncapped. Therefore, any residual amount of radioactive drug or biologically contaminated blood can come into direct contact with the radiation shield of the pig and cause unsuspected contamination of the radiation shield. Consequently, subsequent doses of radiopharmaceuticals may be distributed in radiopharmaceutical pigs that are contaminated with biological and radioactive contaminants. Transporting radiopharmaceutical doses in contaminated pigs thus exposes both hospital staff and patients to potential environmental transmission of blood-borne pathogens, such as Human Immunodeficiency Virus (HIV), Hepatitis B Virus (HBV), and to harmful radioactive materials.

Additionally, because some of the materials used to make the radiation shield, including lead, are very porous, biological contaminants that contaminate the porous material can be very difficult to detect and remove. Often, biological contaminants cannot be detected in a radiation shield that is made of a porous material regardless of the detection methods used. Because biological contaminants often cannot be detected, any potential exposure to biological contaminants would require sterilization and sanitization of the radiation shield. Known processes of sterilizing and sanitizing the pig, including autoclaving, gas sterilization, high pressure steam, and moist heat treatment are often ineffective, time-consuming and expensive. Additionally, because known methods of sterilization and sanitation are often not effective at removing biological contaminants from the radiation shield, the contaminated radiopharmaceutical pig would have to be disposed of.

Radioactive materials can also be very difficult to remove from porous materials. Using known processes to try and remove radioactive contaminants and sanitize the pig is undesirable, because the various processes are often expensive, time-consuming and ineffective. Alternatively, disposing of the contaminated radiopharmaceutical pigs is also not a desirable option, because the radiopharmaceutical pigs are expensive to replace and difficult to dispose of if they contain hazardous materials such as lead.

Another drawback of the above method and apparatus is the exposure to potentially hazardous particles of the exposed radiation shield. The exposed radiation shield creates the potential danger that hazardous particles from the radiation shield will contaminate the environment or the user. Often, a radiopharmaceutical pig with a radiation shield made of lead will create lead dust particles that will remain in the radiopharmaceutical pig, or escape from the radiopharmaceutical pig, and settle on radiopharmacy surfaces. Accordingly, there is the potential danger of human inhalation or ingestion of lead dust from the lead radiation shield. Also, the lead particles could contaminate the syringe and radiopharmaceuticals inserted into the pig, and result in harmful lead particles being unknowingly injected into a patient. To avoid the potential that lead particles would contaminate the environment, the syringe or the radiopharmaceuticals, additional safety procedures and handling equipment that are time-consuming, expensive and not completely effective would need to be implemented. Additionally, if the radiopharmaceutical doses were contaminated with hazardous particles, they would be unuseable, and additional effort and expense would be required to obtain new doses and dispose of the contaminated ones.

The prior art attempted to solve some of the drawbacks described above. One approach involves using a disposable sharps container to encapsulate the syringe containing radiopharmaceuticals before inserting the syringe into the radiopharmaceutical pig. Typically, a disposable sharps container is a two-part assembly including a bottom portion, commonly called a housing, and a top portion, commonly called a cap. The sharps container can be assembled by removably attaching the cap and housing together to create a sealed internal chamber, sized to hold a syringe. In the approach used in the prior art, the sharps container acts as a barrier that prevents potentially hazardous particles from the radiation shield from contaminating the syringe or radiopharmaceuticals, and prevents biological and radioactive contaminants on the spent syringe from contaminating the radiation shield.

Once the syringe containing radiopharmaceuticals is ready to be transported, it is placed into the bottom portion, or housing, of the sharps container. The cap is then removably attached to the housing, thereby causing the syringe to be contained in the sealed internal chamber of the assembled sharps container. The sharps container and the syringe it contains are then inserted into the internal chamber of a radiopharmaceutical pig similar to the one described above.

The radiopharmaceutical pig is then assembled and transported to the desired destination, where it is disassembled when the radiopharmaceutical is needed. Once the pig is disassembled, the cap of the disposable sharps container is removed from the housing, allowing the user access to the syringe. The syringe is then removed while the housing of the disposable sharps container remains in the lower portion of the radiopharmaceutical pig. The syringe is then used for its intended purpose and the contaminated spent syringe is placed back into the housing of the sharps container that remained in the lower portion of the pig. The cap of the sharps container is then placed back onto the housing of the sharps container, thereby encapsulating the contaminated spent syringe. The pig is then assembled with the sharps container and contaminated spent syringe inside the internal chamber of the pig. The assembled pig is then transported into the proper destination for disposal of the sharps container and contaminated spent syringe.

Alternatively, the method described above can be modified to transport the syringe containing radiopharmaceuticals without it being encapsulated in a sharps container. Instead, the sharps container is either included in the same shipping container as the assembled radiopharmaceutical pig or it is obtained through alternative means. Once the syringe has been used or spent it is placed into the bottom portion or housing of the sharps container and the cap is removably attached to the housing, encapsulating the syringe. The sharps container containing the spent syringe is then placed into the bottom portion of the radiopharmaceutical pig. The pig is then assembled and transported to the proper location for disposal of the sharps container and contaminated spent syringe. Using the radiopharmaceutical pig apparatus and methods described above also has certain drawbacks.

One such drawback is potential contamination that results if the user of the radiopharmaceutical pig does not use the disposable sharps container to contain the syringe either before or after its use. Often, users of the radiopharmaceutical pig forget to use the disposable sharps container. When the unused syringe is placed into the lower portion of the pig without the housing of the sharps container, hazardous particles from the radiation shield, like lead dust, can contaminate the syringe and the radiopharmaceuticals it contains. As mentioned above, the radiation shield is typically made of elemental lead, which is a hazardous material. Not using the disposable sharps container to contain the syringe before inserting it into the radiopharmaceutical pig creates the potential that the radiopharmaceutical doses are contaminated with hazardous particles. To avoid possible injury to patients or hospital staff, the radiopharmaceutical doses would need to be discarded and replaced with uncontaminated doses.

Another problem arises if the contaminated spent syringe is placed into the lower portion of the pig without the housing of the sharps container. The residual amount of radiopharmaceuticals and biological contaminants on the spent syringe would very likely come into direct contact with the radiation shield of the radiopharmaceutical pig, and would require expensive and time-consuming cleaning and sterilization of the radiation shield. Additionally, if the radiation shield could not be properly cleaned or sterilized, the contaminated radiopharmaceutical pig would need to be disposed of, resulting in additional expense. Therefore, the method and apparatus described in the prior art eventually results in contamination of the radiation shield of radiopharmaceutical pig, which can be difficult, to impossible, to clean, not to mention expensive and time-consuming.

Additionally, another drawback of the apparatus and method described above is the environmental contamination that can occur because the potentially hazardous particles from the radiation shield are exposed to the environment. When the pig is unassembled, the radiation shield and any loose particles of the radiation shield are exposed to the environment. Hazardous particles, such as lead dust, may escape from the inner chamber of the pig, contaminating the environment and exposing individuals in the vicinity to potentially serious harm. To try to minimize the potentially serious harm that would result from exposure to hazardous particles, such as lead dust, additional safety procedures and handling equipment that are time-consuming, expensive, and not completely effective would need to be implemented.

Accordingly, there exists a need for an improved radiopharmaceutical pig that prevents particles from the radiation shield from contaminating the syringe, the radiopharmaceuticals or the environment, and that prevents biological or radioactive contaminants from contaminating the radiation shield or the environment. The present invention fulfills this need.

SUMMARY OF THE INVENTION

Briefly, and in general terms, the present invention resides in an improved method and apparatus for transporting a container, typically a syringe, containing radioactive material. Advantageously, the present invention provides an apparatus and method that prevents potentially hazardous particles from the radiation shield of a radiopharmaceutical pig from contaminating the radiopharmaceutical container or the environment. The method and apparatus of the present invention also prevents the radiation shield of the radiopharmaceutical pig from being contaminated by the biological or radioactive contaminants on the spent syringe. Additionally, the present invention provides for an apparatus for transporting radiopharmaceuticals that can be quickly and inexpensively cleaned and sanitized.

More specifically, by way of example and not limitation, in a presently preferred embodiment, the apparatus of the present invention forms a radiopharmaceutical pig with an upper portion that can be removably secured to its lower portion. Both portions of the radiopharmaceutical pig include an exterior shell, a radiation shield, a non-porous lining, and an interior surface that defines an internal chamber. The exterior shell of the upper portion and lower portion surround the radiation shield, the non-porous lining, and the internal chamber of the upper portion and the lower portion, respectively. Additionally, the radiation shield of the upper portion and lower portion surround the non-porous lining and the internal chamber of the upper portion and the lower portion, respectively. The non-porous lining of the upper portion and lower portion surrounds the internal chamber.

The non-porous lining covers the radiation shield and prevents hazardous particles from the radiation shield from contaminating the user or environment. By preventing hazardous particles from the radiation shield from contaminating the environment, the apparatus of the present invention allows the contaminated syringe to be transported to the disposal area, where it can be handled by users without using time-consuming and expensive techniques required to handle hazardous materials. This saves the hospital the in-house handling and disposal costs associated with the need to use special techniques when dealing with hazardous materials, like lead. The non-porous liner also allows the internal chamber of the radiopharmaceutical pig to be cleaned and sterilized quickly and inexpensively.

In another detailed aspect of a preferred embodiment of the present invention, the apparatus additionally includes a removable, disposable container having a cap and housing. The internal chamber of the assembled radiopharmaceutical pig is also sized to fit the disposable container and the assembled, disposable container is sized to contain a syringe. By placing the syringe containing radiopharmaceuticals into the housing and then placing the cap on the housing, the syringe is encapsulated by the disposable container. The container and the syringe it holds are then placed in the internal chamber of the bottom portion of the radiopharmaceutical pig and the pig is assembled by removably attaching the top portion of the radiopharmaceutical pig to the bottom portion containing the container and syringe.

In yet another detailed aspect of a preferred embodiment of the present invention, the exterior shell and the non-porous lining of the upper portion together form one continuous piece that encapsulates the radiation shield of the upper portion. Additionally, the exterior shell and the non-porous lining of the lower portion together form one continuous piece that encapsulates the radiation shield of the lower portion.

In yet another detailed aspect of a preferred embodiment of the present invention, the non-porous lining of the upper portion and lower portion is made of latex or vinyl paints, lacquers, rubbers, varnishes, epoxy resins, plastics, elastomers, urethane, metals, steels, metal composites, Teflon or silicon.

In yet another detailed aspect of a preferred embodiment of the present invention, the non-porous lining of the upper portion and lower portion is made of any combination of latex or vinyl paints, lacquers, rubbers, varnishes, epoxy resins, plastics, elastomers, urethane, metals, steels, metal composites, Teflon and silicon.

In a presently preferred method of the present invention, by way of example and not limitation, a container, typically a syringe, is filled with a radiopharmaceutical. The container and the radiopharmaceutical it contains are then inserted into the internal chamber of the radiopharmaceutical pig. The internal chamber of the pig is surrounded by a non-porous lining that is located between the internal cavity of the radiopharmaceutical pig and a radiation shield. The non-porous lining is surrounded by the radiation shield and the radiation shield is surrounded by an exterior shell of the radiopharmaceutical pig. The radiopharmaceutical pig is then assembled by securing the upper and lower portions of the radiopharmaceutical pig together. Once the radiopharmaceutical pig is assembled, the radiation shield encapsulates the container that resides in the internal chamber of the pig.

An alternative method of the present invention begins with filling a syringe with a radiopharmaceutical. The syringe is then inserted into a housing that covers the bottom portion of the syringe. The housing and syringe are then inserted into the internal chamber of the pig together. The internal chamber of the radiopharmaceutical pig is sized to accept the housing and syringe. The radiopharmaceutical pig is then assembled by securing the upper and lower portion of the radiopharmaceutical pig together. Once the radiopharmaceutical pig is assembled, the radiation shield of the pig encapsulates the housing and the syringe.

In another detailed aspect of a preferred method of the present invention, a cap is placed on the housing after the syringe and housing are inserted into the internal chamber of the radiopharmaceutical pig. The cap and housing together encapsulate the syringe and protect the container and radiopharmaceuticals from becoming contaminated by particles from the radiation shield. The cap and housing also protects the radiation shield and environment from becoming contaminated with biological or radioactive contaminants on the spent syringe.

Other features and advantages of the present invention will become apparent from the following description of the preferred embodiments, taken in conjunction with the accompanying drawings, which illustrate, by way of example, the principles of the invention.

BRIEF DESCRIPTION OF THE DRAWINGS

The invention will now be described with reference to the presently preferred embodiments shown in the drawings, which are provided only as examples to illustrate the principles of the invention. The invention is not limited to the embodiments shown, and variations will be apparent to those skilled in the art. The embodiments are not shown or described in more detail than necessary to describe the invention, and the manner and process of making and using it, to those skilled in the art.

In the drawings.

DESCRIPTION OF THE PREFERRED EMBODIMENTS

The present invention provides for an improved apparatus and method for transporting radiopharmaceuticals. The improved method and apparatus of the present invention described herein provide a number of significant advantages. By way of example only, some of the advantages of the present invention include avoiding biological or radioactive contamination of the radiation shield of radiopharmaceutical pig, preventing environmental contamination of potentially hazardous particles from the radiation, and providing an apparatus for transporting radiopharmaceuticals that can be quickly and inexpensively cleaned and sanitized.

Figure 1:
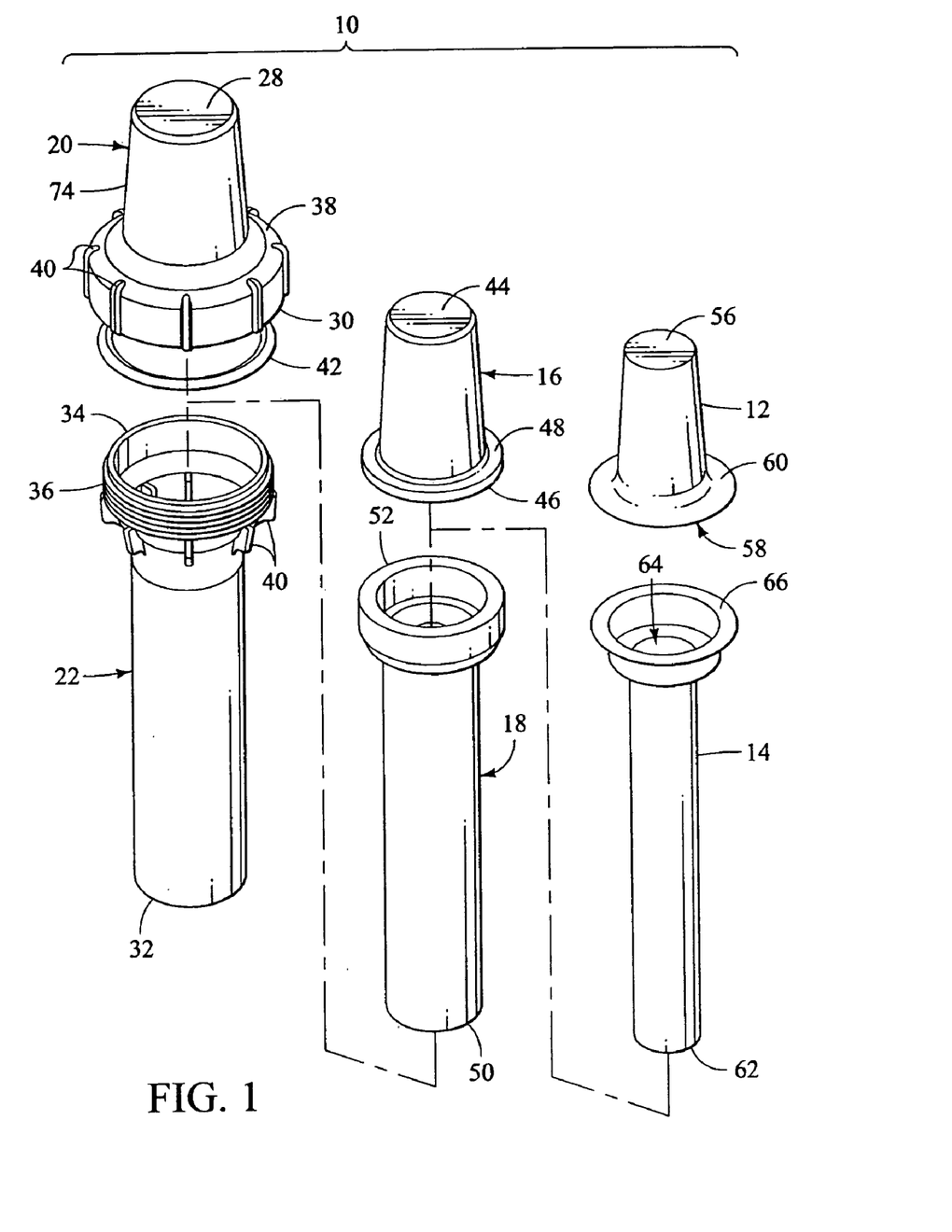
FIG. 1 is a perspective view of the exploded apparatus for transporting radiopharmaceuticals, in accordance with the present invention, showing the relative placement of the exterior shell, radiation shield, and the non-porous lining.

Referring now to the drawings, and particularly to FIG. 1, there is shown, by way of example and not limitation, an apparatus for transporting radiopharmaceuticals that is typically called a radiopharmaceutical pig, indicated generally by reference numeral 10, in accordance with the a preferred embodiment of the present invention. The structural components of radiopharmaceutical pig 10 include a non-porous upper lining 12 and a non-porous lower lining 14 that nest within an upper radiation shield 16 and a lower radiation shield 18, respectively. The upper shield 16 and the lower shield 18 nest within an upper exterior shell 20 and a lower exterior shell 22, respectively. The interior surface of upper lining 12 and lower lining 14 that does not contact either the upper shield 16 or the lower shield 18 defines the bounds of an internal chamber that contains the radiopharmaceuticals. The internal chamber of the upper shield 16 is surrounded by the upper lining 12. The internal chamber of the lower shield 18 is surrounded by the lower lining 14.

The upper lining 12 and the lower lining 14 of the present invention are preferably made of a durable plastic, but may be made of any non-porous material that prevents contamination of the radiation shield. Examples of material that the upper lining 12 and lower lining 14 might be made of include, but are not limited to, oil-based, latex or vinyl paints, lacquers, rubbers, varnishes, epoxy resins, plastics, elastomers, urethane, metals, steels, metal composites, Teflon, silicon and any non-porous material known to those skilled in the art.

The upper lining 12 and lower lining 14 are preferably made of a durable material, so the internal chamber of the radiopharmaceutical pig 10 can be repeatedly cleaned and sanitized without damage or wear to the linings. Therefore, if either the upper lining 12 or the lower lining 14 become contaminated with blood-borne pathogens or radioactive material, they can quickly and easily be cleaned with sodium hypochlorite or gluteraldehyde. Without the upper lining 12 and lower lining 14, a more expensive and time consuming cleaning process would be required to clean the upper radiation shield 16 and the lower radiation shield 18. Additionally, if the upper shield 16 and a lower shield 18 are made of a porous material, it is difficult, to impossible, to satisfactorily clean and sanitize them.

The upper lining 12 and lower lining 14 of the radiopharmaceutical pig 10 also allows the internal chamber of the radiopharmaceutical pig 10 to be cleaned and sterilized without requiring the time and expense associated with cleaning and sterilizing the upper radiation shield 16 and the lower radiation shield 18. Additionally, the upper lining 12 covers the upper radiation shield 16 and the lower lining 14 covers the lower radiation shield 18, preventing particles from the upper radiation shield 16 and the lower radiation shield 18, such as lead dust, from contaminating the environment. The upper lining 12 and lower lining 14 also prevents the radiopharmaceutical doses that are placed into the inner chamber of the pig from becoming contaminated by particles from the upper radiation shield 16 and the lower radiation shield 18.

The upper lining 12 has a generally tubular, cup-like shape, featuring a closed end 56 and an open end 58, with a circumferential ridge 60. The lower lining 14 has a generally tubular, elongated cup-like shape featuring a closed end 62 and an open mating end 64 and a ridge 66. The upper lining 12 and the lower lining 14 have internal chambers or cavities sized to accept a syringe, or a container that can accommodate a syringe.

The external dimensions of the upper lining 12 and lower lining 14 are sized so that they nest within the upper shield 16 and lower shield 18, respectively. The circumferential ridge 60 on the mating end 58 of the upper lining 12 abuts the mating end 64 of the lower lining 14 when the radiopharmaceutical pig 10 is assembled.

The upper shield 16 has a generally tubular, cup-like shape featuring a closed end 44 and an open end 46 with a circumferential flange 48. The lower shield 18 has a generally tubular, elongated cup-like shape, featuring a closed end 50 and an open mating end 52. The upper radiation shield 16 and lower radiation shield 18 have internal chambers or cavities sized to accept their respective upper lining 12 and lower lining 14.

The external dimensions of the upper shield 16 and lower shield 18 are sized so that they nest within the upper shell 20 and lower shell 22, respectively. The upper shield 16 and the lower shield 18 are preferably constructed of elemental lead, but may be constructed of any material that prevents more than a minimal amount of radiation from the radiopharmaceutical from going through either upper shield 16 or lower shield 18.

The exterior upper shell 20 of the radiopharmaceutical pig 10 has a generally tubular, cup-like shape, a closed end 28 and an open mating end 30 with internal threads. Similarly, the exterior lower shell 22 has a generally tubular, elongated cup-like shape, featuring a closed end 32 and an open mating end 34 with external threads 36. The mating end of the upper shell 20 has a flange 38 to provide for the internal threads that engage the external threads located on the mating end 34 of the lower shell 22. The upper shell 20 and lower shell 22 have interior surfaces sized to accept radiation shield 16 and radiation shield 18, respectively. External anti-roll ridges 40 are circumferentially located adjacent to the mating ends 30 and 34 of the upper shell 20 and the lower shell 22.

The upper shell 20 and lower shell 22 are preferably constructed from an ABS plastic, such as ABS Sinkral B-54 acrylontrile butadiene styrene from Enichem America, Inc., 1211 Avenue of the Americas, New York, N.Y. 11436. ABS plastic material is more durable than other plastics. Accordingly, both upper shell 20 and lower shell 22 are less likely to crack or fracture, giving the radiopharmaceutical pig 10 a longer, useful life and advantageously reducing expenses by reducing the number of broken radiopharmaceutical pigs that need to be replaced. Additionally, upper shell 20 and lower shell 22 prevent potentially harmful particles from the upper shield 16 and a lower shield 18 from contaminating the user or the environment. In accordance with the present invention, the upper shell 20 and lower shell 22 can be made of any durable material, including, but not limited to, plastics, metals, stainless steel, metal composites or any durable material commonly used by those skilled in the art.

An "O" ring 42 fits between the upper shell 20 and the lower shell 22 to provide an air and fluid tight seal. The "O" ring is preferably made from a nitrile rubber, such as Nitrile, from DWA Industrial Products, Inc., 9780 Variel Avenue, Chatsworth, Calif. 91311. However, the "O" ring could be made from any other material suitable for providing an effective seal.

Figure 2:
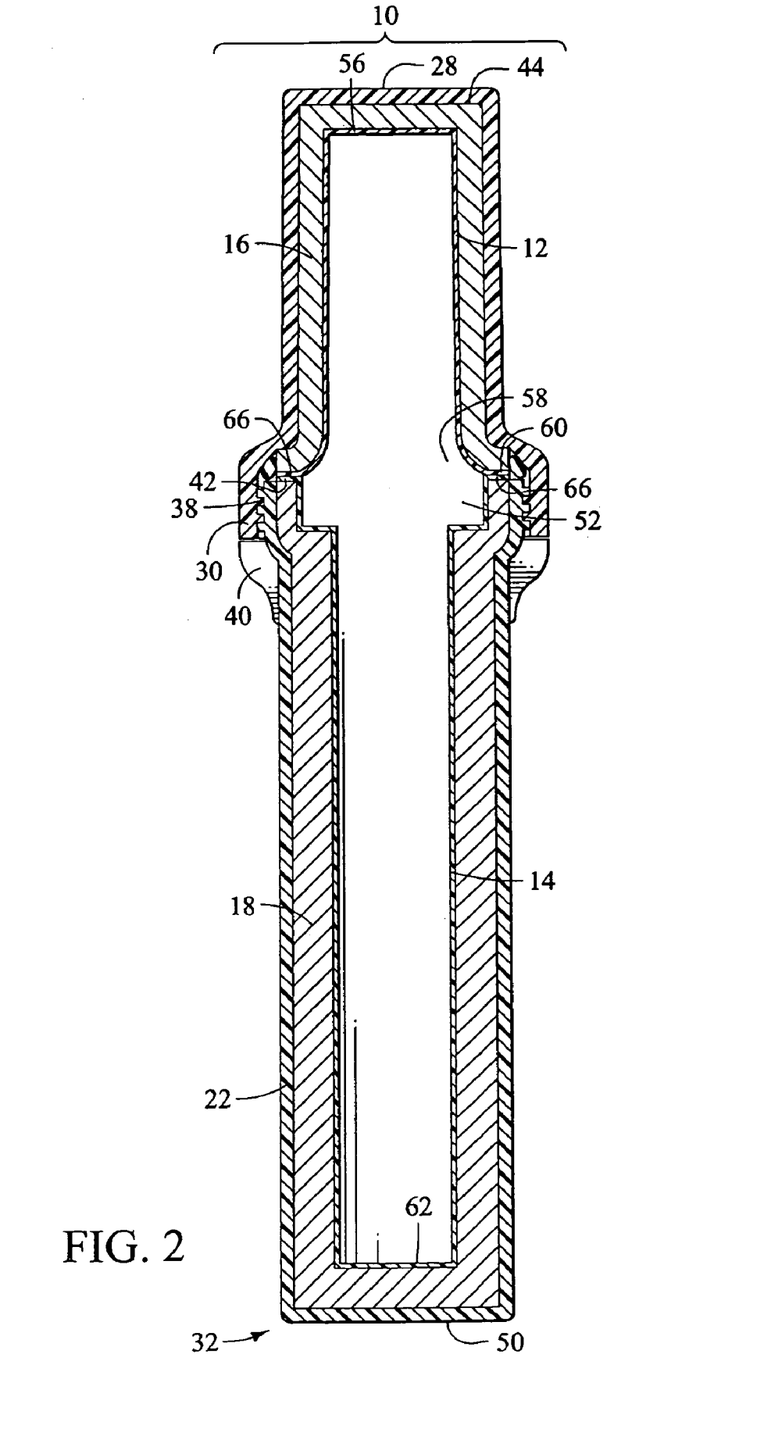
FIG. 2 is a cross-sectional elevational view of the apparatus for transporting radiopharmaceuticals of FIG. 1.

Referring now to FIG. 2, a cross-sectional view of the radiopharmaceutical pig of FIG. 1, described above, is shown. FIG. 2 shows the internal chamber of the radiopharmaceutical pig being empty.

Figure 3:
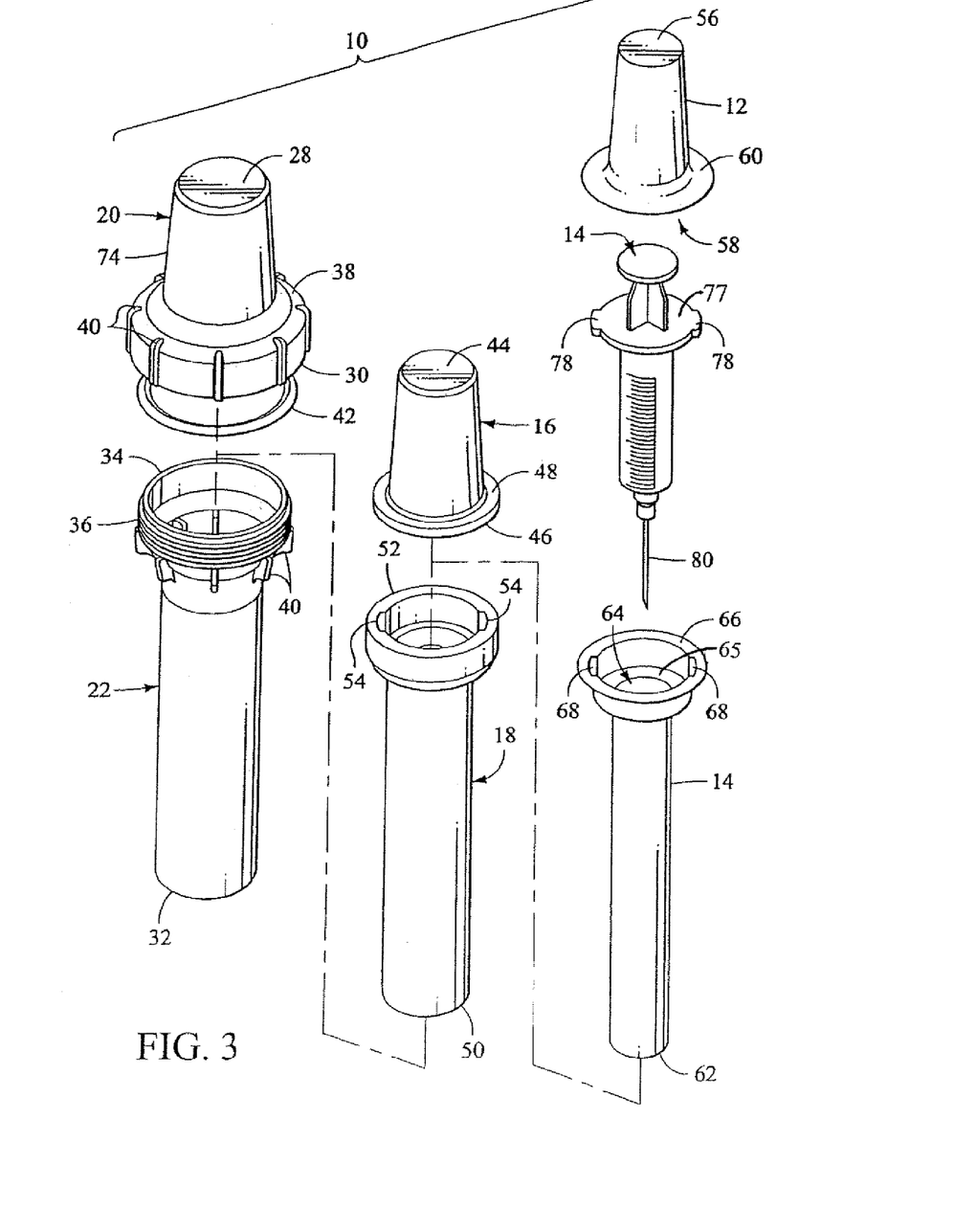
FIG. 3 is a perspective view of an alternative embodiment of the exploded apparatus for transporting radiopharmaceuticals of the present invention showing the relative placement of the exterior shell, radiation shield, and the non-porous lining.

Referring now to FIG. 3, there is shown, by way of example only, the components of a radiation-shielded container, in accordance with another preferred embodiment of the present invention. The structural components of the radiopharmaceutical pig include an upper lining 12 and a lower lining 14 that nest within an upper radiation shield 16 and a lower radiation shield 18, respectively. The upper shield 16 and the lower shield 18 nest within an upper exterior shell 20 and a lower exterior shell 22, respectively. Additionally, in FIG. 3, a syringe 80 with a plunger 14 and protrusions 78 is shown, by way of example only, as one device that could be used with a preferred embodiment of the present invention to contain radiopharmaceuticals. In accordance with the present invention, other devices that are known to those skilled in the art to contain radiopharmaceuticals can also be used.

The radiopharmaceutical pig shown in FIG. 3 is identical to the radiopharmaceutical pig shown in FIG. 1 and discussed above, except that the radiopharmaceutical pig of FIG. 3 additionally contains a pair of cutouts 68 on the lower lining 62 and a pair of cutouts 54 on the lower shield 50. The protrusions 78 of the syringe 80 mate with the pair of cutouts 68 on the lower lining 62 and the pair of cutouts 54 on the lower shield 50. The protrusions 78 of the syringe 80 and the cutouts 68 and 54 prevent the syringe 80 from rotating about its longitudinal axis.

Figure 4:
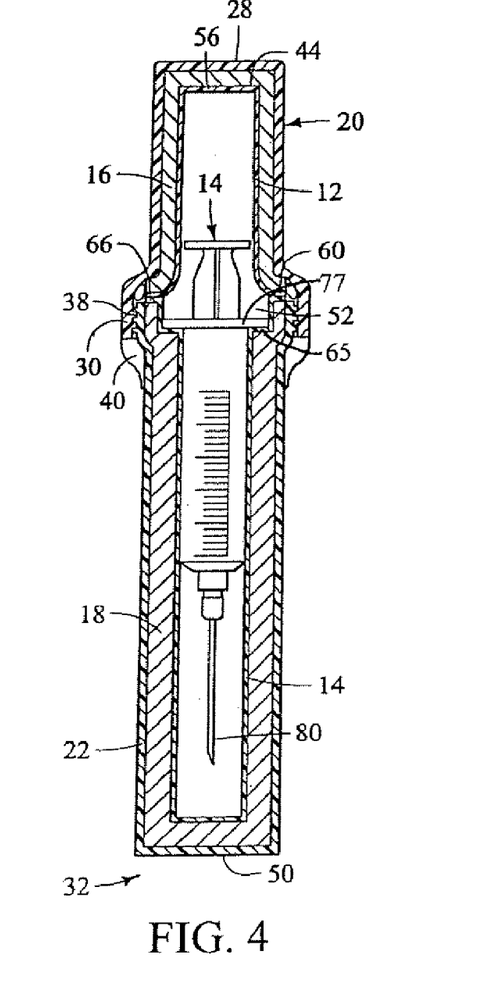
FIG. 4 is a cross-sectional elevational view of the apparatus for transporting radiopharmaceuticals of FIG. 3.

FIG. 4 shows a cross-sectional view of the assembled radiopharmaceutical pig of FIG. 3 with the syringe received in the lower lining. As shown, the diameter of the internal chamber or cavity of the lower lining is sized to receive the syringe with a close fit, and an annular shoulder 65 is formed in the lower lining adjacent its open end 64. The syringe has a flange 77 that abuts against the shoulder in the lower lining to serve as a stop, engaging the syringe to limit its insertion into the lower lining and keeping the syringe spaced from the closed end 62 of the lower lining 14.

Figure 5:
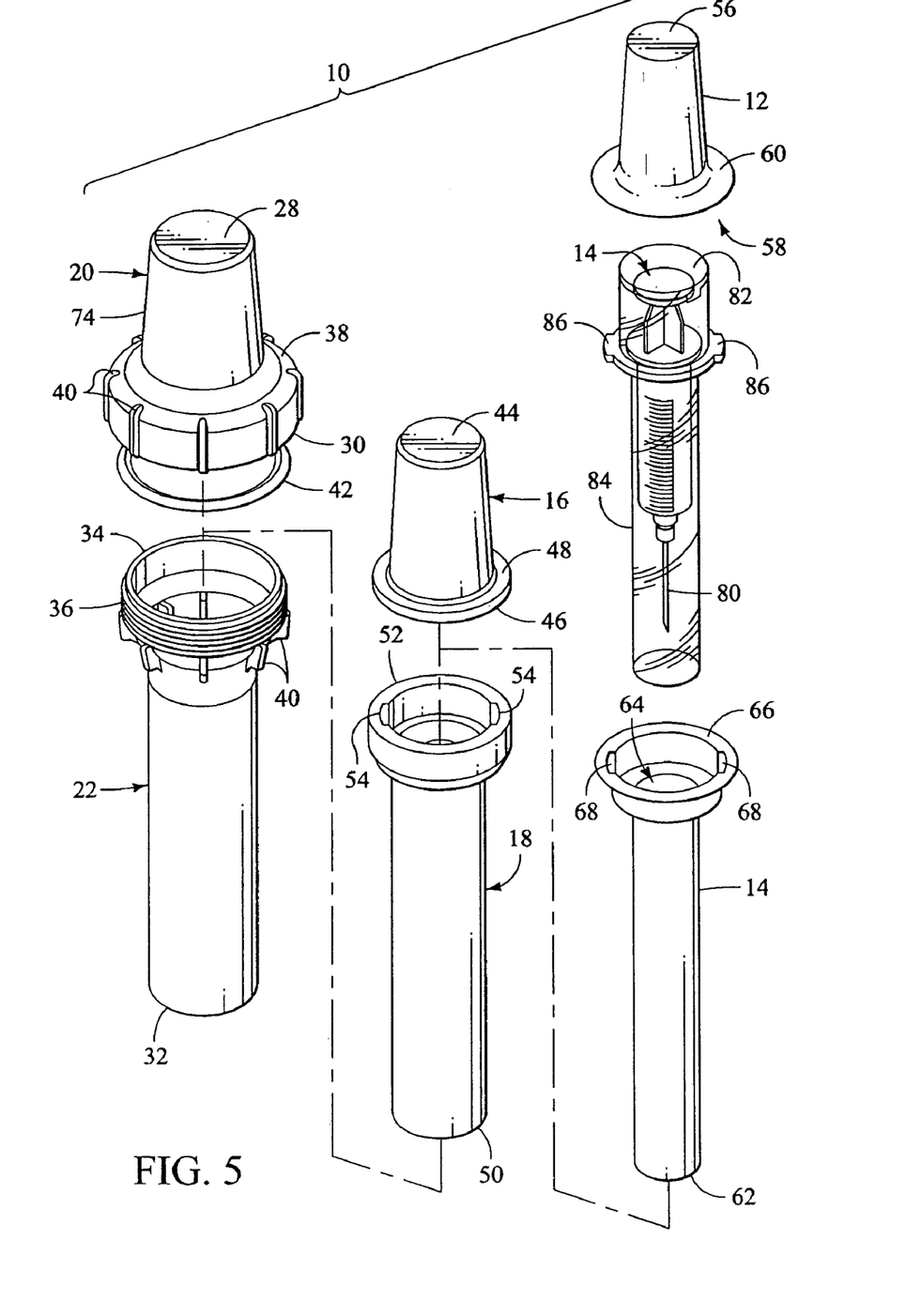
FIG. 5 is a perspective view of an alternative embodiment of the exploded apparatus for transporting radiopharmaceuticals of the present invention showing the relative placement of the exterior shell, radiation shield, and the non-porous lining.

Referring now to FIG. 5, there is shown, by way of example only, the components of a radiopharmaceutical pig 10 in accordance with yet another preferred embodiment of the present invention. The structural components of the radiopharmaceutical pig include an upper lining 12 and a lower lining 14 that nest within an upper radiation shield 16 and a lower radiation shield 18, respectively. The upper shield 16 and the lower shield 18 each nest within an upper shell 20 and a lower shell 22, respectively. Additionally, in FIG. 3 there is shown a housing 84 with protrusions 86 and a cap 82, by way of example only, as a disposable container that could be used with the present invention to house the syringe containing the radiopharmaceuticals. In accordance with the present invention, other disposable containers known to those skilled in the art could also be used.

The preferred embodiment shown in FIG. 5 is identical to the embodiment shown in FIG. 3, except that FIG. 5 shows an embodiment wherein the syringe 80 is completely encapsulated by a housing 84 and a cap 82 which include protrusions 86. Additionally, unlike the syringe 80 shown in FIG. 3, the syringe 80 in FIG. 5 does not have protrusions 78 that mate with the cutouts 68 on the lower lining 62 and cutouts 54 the lower shield 50. Instead, the embodiment of the present invention shown in FIG. 5 includes a housing 84 with protrusions 86 that mate with the cutouts 68 on the lower lining 14 and the cutouts 54 on the lower shield 50. The protrusions 86 on the container prevent the housing 84 and the syringe 80 that it contains from rotating about its longitudinal axis.

Figure 6:
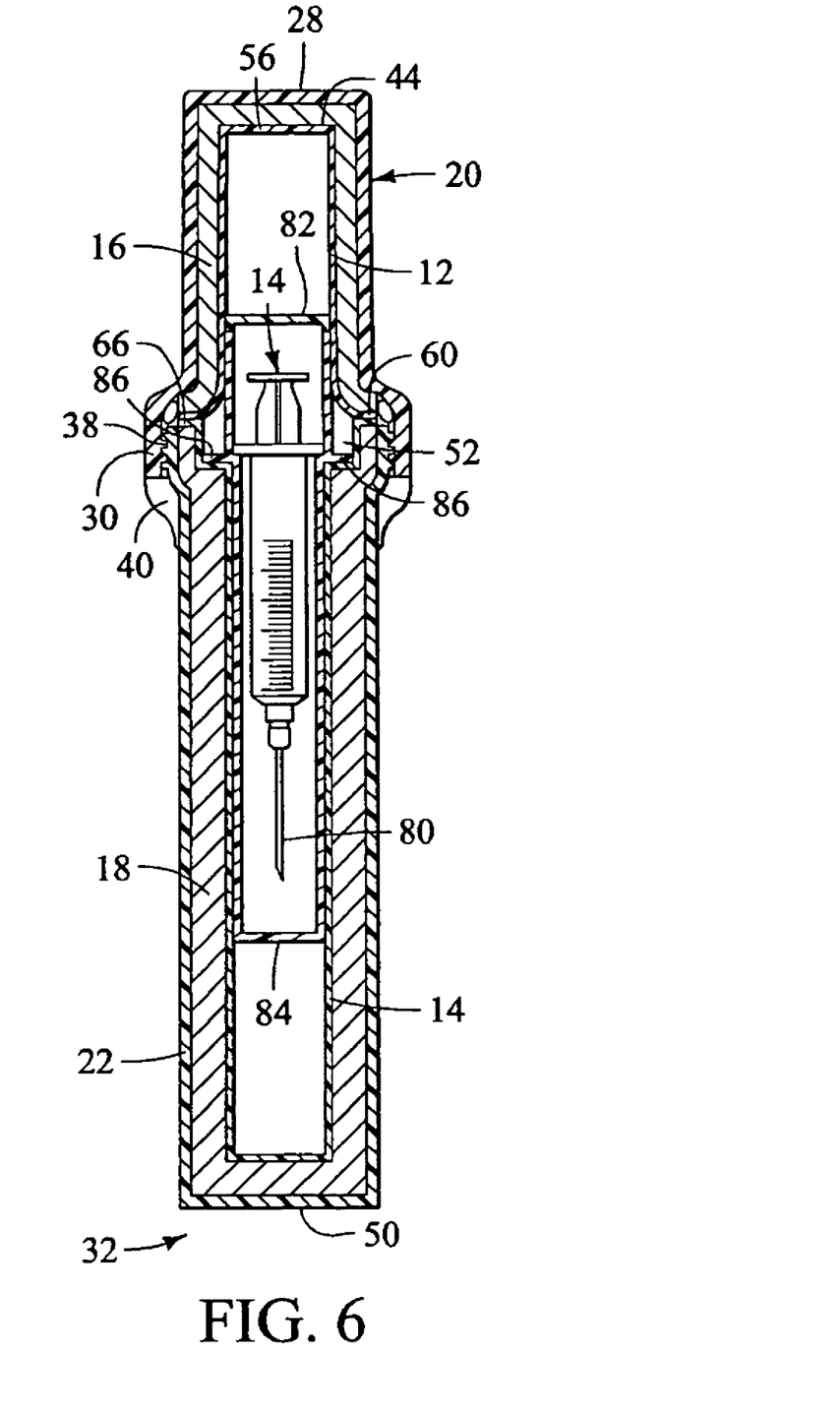
FIG. 6 is a cross-sectional elevational view of the apparatus for transporting radiopharmaceuticals of FIG. 5.

Referring now to FIG. 6, there is shown, by way of example only, a cross-sectional view of the radiopharmaceutical pig shown in FIG. 5. FIG. 6 shows the syringe 80 with plunger 14 inside the housing 84 and cap 82, and the syringe 80 with plunger 14 and the housing 84 and cap 82 inside the internal chamber of the radiopharmaceutical pig 10.

The foregoing detailed description of the present invention is provided for the purposes of illustration and is not intended to be exhaustive or to limit the invention to the precise embodiments disclosed. Accordingly, the scope of the present invention is defined only by the following claims.

We claim:

1. A radiopharmaceutical pig for transporting a radiopharmaceutical syringe comprising:
   an upper portion removably securable to a lower portion, the upper portion and lower portion each including an exterior shell, a radiation shield and a non-porous lining, and defining an internal chamber for the radiopharmaceutical syringe;
   the upper and lower exterior shells, radiation shields and non-porous linings each having an interior surface and an exterior surface, wherein the exterior shell of the upper and lower portions surrounds the radiation shield and the non-porous lining of the upper and lower portions,
   wherein the radiation shield of the upper and lower portions surrounds the non-porous lining of the upper and lower portions,
   wherein the non-porous lining of the upper and lower portions is adhered to the interior surface of the radiation shield of the upper and lower portions, and
   wherein the lower portion of the internal chamber has a closed end and an open end, the lower portion being elongated and configured to engage the radiopharmaceutical syringe to limit its insertion into the internal chamber of the non-porous lining in order to keep the radiopharmaceutical syringe spaced from the closed end of the lower portion of the internal chamber.

2. A radiopharmaceutical pig as defined in claim 1, wherein the internal chamber is sized to fit a syringe.

3. A radiopharmaceutical pig as defined in claim 1, wherein the upper and lower exterior shells comprise a plastic.

4. A radiopharmaceutical pig as defined in claim 1, wherein the upper and lower exterior shells comprise a durable material.

5. A radiopharmaceutical pig as defined in claim 1, wherein the upper and lower radiation shields comprise lead.

6. A radiopharmaceutical pig as defined in claim 1, wherein the upper and lower radiation shields comprise a metal.

7. A radiopharmaceutical pig as defined in claim 1, wherein the upper and lower non-porous linings comprise a plastic.

8. A radiopharmaceutical pig as defined in claim 1, wherein the upper and lower non-porous linings are cleanable.

9. A radiopharmaceutical pig as defined in claim 1, wherein the upper and lower non-porous linings comprise a paint.

10. A radiopharmaceutical pig as defined in claim 1, wherein the upper ad lower exterior shells substantially enclose the exterior surface of the upper and lower radiation shields.

11. A radiopharmaceutical pig as defined in claim 1, wherein the interior surface of the upper and lower radiation shields is entirely enclosed by the upper and lower non-porous linings.

12. A radiopharmaceutical pig for transporting a radiopharmaceutical syringe comprising:
    an upper portion removably securable to a lower portion, the upper portion and lower portion each including an exterior shell, a radiation shield and a non-porous lining, and defining a internal chamber for the radiopharmaceutical syringe;
    the upper and lower exterior shells, radiation shields and non-porous linings each having a interior surface and an exterior surface, wherein the exterior shell of the upper and lower portions surrounds the radiation shield and the non-porous lining of the upper and lower portions,
    wherein the radiation shield of the upper and lower portions surrounds the non-porous lining of the upper and lower portions,
    wherein the non-porous lining of the upper and lower portions is a coating that conforms in shape to the interior surface of the radiation shield of the upper and lower portions, and
    wherein the lower portion of the internal chamber has a closed end and an open end, the lower portion being elongated and configured to engage the radiopharmaceutical syringe to limit its insertion into the internal chamber of the non-porous lining in order to keep the radiopharmaceutical syringe spaced from the closed end of the lower portion of the internal chamber.

13. A radiopharmaceutical pig for transporting a radiopharmaceutical syringe comprising:
    an upper portion removably securable to a lower portion, the upper portion and lower portion each including an exterior shell, a radiation shield and a non-porous lining, and defining an internal chamber for the radiopharmaceutical syringe;
    the upper and lower exterior shells, radiation shields and non-porous linings each having an interior surface and an exterior surface, wherein the exterior shell of the upper and lower portions surrounds the radiation shield and the non-porous lining of the upper and lower portions,
    wherein the radiation shield of the upper and lower portions surrounds the non-porous lining of the upper and lower portions,
    wherein the non-porous lining of the upper and lower portions is adhered to the interior surface of the radiation shield of the upper and lower portions, and
    wherein the lower portion of the internal chamber has a closed end and an open end, the lower portion being elongated and configured to hold a radiopharmaceutical syringe, the lower portion including a shoulder adjacent to the open end that that engages the radiopharmaceutical syringe to limit its insertion into the internal chamber of the non-porous lining in order to keep the radiopharmaceutical syringe spaced from the closed end of the lower portion of the internal chamber.

14. A method for transporting a radiopharmaceutical pig containing a radiopharmaceutical syringe, the method comprising;
    providing an upper exterior shell, an upper radiation shield, and an upper non-porous lining, wherein an interior surface of the upper non-porous lining defines an upper portion of an internal chamber, and wherein the upper non-porous lining is adhered to an interior surface of the upper radiation shield;
    providing a lower exterior shell, a lower radiation shield, and a lower non-porous lining, wherein an interior surface of the lower non-porous lining defines a lower portion of an internal chamber, wherein the lower non-porous lining is adhered to an interior surface of the lower radiation shield, wherein the lower portion of the internal chamber includes a closed end and an open end, and wherein the lower portion is elongated and configured to engage the radiopharmaceutical syringe to limit its insertion into the internal chamber of the non-porous lining in order to keep the radiopharmaceutical syringe spaced from the closed end of the lower portion of the internal chamber; and attaching the upper exterior shell, upper radiation shield, and upper non-porous lining to the lower exterior shell, lower radiation shield, and lower non-porous lining.

15. The method as defined in claim 14, further comprising placing the radiopharmaceutical pig into a shipping container for transportation to the location for use.

16. The method as defined in claim 15, further comprising transporting the radiopharmaceutical pig to the location for use.

17. The method as defined in claim 16, further comprising placing a label having information that is useful to the user or patient on the radiopharmaceutical pig before transporting the radiopharmaceutical pig to the location for use.

18. The method as defined in claim 17, wherein the information is selected from a group consisting of a patient's name, a production lot number, an expiration date for the radioactive material, a quantity of the radioactive material, a name of an intended medical procedure, a half life for the radioactive material, a bar code, and a color code.

19. The method as defined in claim 14, wherein assembling the radiopharmaceutical pig includes screwing one portion of the radiopharmaceutical pig to another portion of the radiopharmaceutical pig.

20. A method for transporting a radiopharmaceutical pig containing a radiopharmaceutical syringe, the method comprising:

providing an upper exterior shell, an upper radiation shield, and an upper non-porous lining, wherein an interior surface of the upper non-porous lining defines an upper portion of an internal chamber, and wherein the upper non-porous lining is a coating that conforms in shape to an interior surface of the upper radiation shield;

providing a lower exterior shell, a lower radiation shield, and a lower non-porous lining, wherein an interior surface of the lower non-porous lining defines a lower portion of an internal chamber, wherein the lower non-porous lining is a coating that conforms in shape to an interior surface of the lower radiation shield, wherein the lower portion of the internal chamber includes a closed end and an open end, and wherein the lower portion is elongated and configured to engage the radiopharmaceutical syringe to limit its insertion into the internal chamber of the non-porous lining in order to keep the radiopharmaceutical syringe spaced from the closed end of the lower portion of the internal chamber;

placing a radiopharmaceutical syringe into the internal chamber; and attaching the upper exterior shell, upper radiation shield, and upper non-porous lining to the lower exterior shell, lower radiation shield, and lower non-porous lining.

* * * * *

UNITED STATES PATENT AND TRADEMARK OFFICE
CERTIFICATE OF CORRECTION

PATENT NO.        : 7,268,359 B2
APPLICATION NO.   : 11/184291
DATED             : September 11, 2007
INVENTOR(S)       : Monty Mong Chen Fu et al.

It is certified that error appears in the above-identified patent and that said Letters Patent is hereby corrected as shown below:

At column 11, line 51, "ad" should be -- and --.

At column 11, line 63, "a" should be -- an --.

At column 11, line 66, "a" should be -- an --.

Signed and Sealed this

Twenty-ninth Day of April, 2008

JON W. DUDAS
*Director of the United States Patent and Trademark Office*

(12) EX PARTE REEXAMINATION CERTIFICATE (8267th)
United States Patent
Fu et al.

(10) Number: US 7,268,359 C1
(45) Certificate Issued: May 24, 2011

(54) APPARATUS AND METHOD FOR TRANSPORTING RADIOPHARMACEUTICALS

(76) Inventors: Monty Mong Chen Fu, Chatsworth, CA (US); Bing Bing Zhu, Stevensons Ranch, CA (US)

Reexamination Request:
No. 90/009,218, Jul. 16, 2008

Reexamination Certificate for:
Patent No.: 7,268,359
Issued: Sep. 11, 2007
Appl. No.: 11/184,291
Filed: Jul. 18, 2005

Related U.S. Application Data

(63) Continuation of application No. 10/310,353, filed on Dec. 4, 2002, now abandoned.
(60) Provisional application No. 60/338,355, filed on Dec. 5, 2001.

(51) Int. Cl.
*G21F 5/00* (2006.01)

(52) U.S. Cl. .................. 250/507.1; 250/506.1; 206/365
(58) Field of Classification Search .................. None
See application file for complete search history.

(56) References Cited

U.S. PATENT DOCUMENTS

5,831,271 A  11/1998  Okano et al.

RE36,693 E  5/2000  Reich

*Primary Examiner*—Margaret Rubin (57) ABSTRACT

A method and apparatus for transporting radiopharmaceuticals. Typically, the apparatus is a two-part assembly, each part having an exterior shell, a radiation shield and a non-porous lining. Additionally, the assembled apparatus has a sealed internal chamber suitable for carrying a syringe or a sharps container containing a syringe. The internal chamber of the radiopharmaceutical pig is lined with a non-porous lining, typically a durable plastic, that prevents contamination of the radiopharmaceutical doses, the radiation shield, or the environment. Additionally, the non-porous lining can be quickly and easily cleaned and sterilized, avoiding the often difficult, to impossible, task of cleaning and sterilizing the radiation shield of the radiopharmaceutical pig. The non-porous lining is surrounded by a radiation shield that is typically comprised of elemental lead. The radiation shield prevents radiation from the radiopharmaceutical from contaminating the user or environment. The radiation shield is surrounded by an exterior shell that absorbs impact and prevents the radiopharmaceutical pig from breaking. Additionally, the exterior shell prevents environmental exposure to the potentially hazardous material of the radiation shield. Generally, a method of transporting a radiopharmaceutical by filling the container with a radiopharmaceutical, inserting the container into the internal chamber of the radiopharmaceutical pig having a non-porous lining, and assembling the radiopharmaceutical pig so the that the container is in the internal chamber and is encapsulated by the radiation shield, is also provided.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-8 and 10-20 are cancelled.
Claim 9 was not reexamined.

* * * * *